United States Patent
Fujimori et al.

(10) Patent No.: US 6,491,942 B1
(45) Date of Patent: Dec. 10, 2002

(54) SUPPOSITORIES

(75) Inventors: Tomoko Fujimori, Tokyo (JP); Kimiko Sugita, Tokyo (JP)

(73) Assignee: Taisho Pharmaceutical Co., Ltd. (JP)

( * ) Notice: Subject to any disclaimer, the term of this patent is extended or adjusted under 35 U.S.C. 154(b) by 0 days.

(21) Appl. No.: 09/830,431

(22) PCT Filed: Nov. 17, 1999

(86) PCT No.: PCT/JP99/06405
§ 371 (c)(1),
(2), (4) Date: Apr. 26, 2001

(87) PCT Pub. No.: WO00/29026
PCT Pub. Date: May 25, 2000

(30) Foreign Application Priority Data

Nov. 17, 1998 (JP) .......................................... 10-326251

(51) Int. Cl.[7] .......................... A61F 9/02; A61F 13/00; A61F 2/00; A61K 9/48; A61K 9/36
(52) U.S. Cl. ........................ 424/436; 424/422; 424/423; 424/451; 424/480; 514/772.4; 514/778
(58) Field of Search .................. 424/422, 423, 424/436, 464, 468, 480, 451; 514/772.4, 778

(56) References Cited

U.S. PATENT DOCUMENTS

| | | | |
|---|---|---|---|
| 4,678,516 A | 7/1987 | Alderman et al. | 106/197.01 |
| 4,695,464 A | 9/1987 | Alderman et al. | 424/449 |
| 5,120,838 A | 6/1992 | Just et al. | 536/90 |
| 5,124,445 A | 6/1992 | Just et al. | 536/84 |

FOREIGN PATENT DOCUMENTS

| | | |
|---|---|---|
| EP | 0177893 | 10/1985 |
| EP | 0457672 | 5/1991 |
| EP | 0770384 | 10/1996 |
| JP | 63-280016 | 11/1988 |
| JP | 1-143825 | 6/1989 |
| JP | 3-223301 | 10/1991 |
| JP | 4-74108 | 3/1992 |
| JP | 6-166614 | 6/1994 |
| JP | 6-227965 | 8/1994 |

OTHER PUBLICATIONS

Ermis, Dilek et al.; Ketoprofen sustained–release suppositories containing hydroxypropylmethylcellulose phthalate in polyethylene glycol bases; 1995 vol. 13 No. 1. pp. 65–71.*

Ermis Dilek et al. Int. J. Pharm., 1995 vol. 13 No. 1, pp. 65–71.

* cited by examiner

Primary Examiner—Thurman K. Page
Assistant Examiner—Humera N. Sheikh
(74) Attorney, Agent, or Firm—Lorusso & Loud

(57) ABSTRACT

The present invention provides a suppository comprising a hydrophobic hydroxypropyl methylcellulose. The present invention is useful as a suppository base which has little interaction with a drug and has an excellent retainability.

7 Claims, No Drawings

SUPPOSITORIES

TECHNICAL FIELD

The present invention relates to suppositories, and more particularly, relates to suppositories which are excellently retainable between the anus and the lower region of the rectum.

BACKGROUND ART

It is known that a suppository, after administered rectally, is disadvantageously spread in the rectum so that the drug is diluted around the affected site. There are reported a number of techniques for inhibition of such spreading, for example, a technique combining metal salts of polyacrylic acid in JP-A-54-26325, a technique combining a mixture of polyacrylic acid and polyvinylpyrrolidone in JP-A-6-40889, a technique combining carboxyvinyl polymers in JP-A-63-280016 and JP-A-1-143825, a technique combining a gel-forming agent such as alkali metal salts of polygum in JP-A-59-55817, a technique combining polyvinyl alcohol, pectin and pullulan in JP-A-61-109710, a technique combining water-swelling clay minerals such as Laponite in JP-A-2-15024, a technique combining water-insoluble absorptive resins such as starch grafted acrylate in JP-A-4-164023, etc.

However, in order to use a suppository as a pharmaceutical preparation, it is necessary to satisfy not only retainability but also many other requirements such as safety, stability and the like. For this reason, acrylate polymers, especially carboxyvinyl polymers, are actually used in many cases.

Carboxyvinyl polymers, when used as a suppository base, have an excellent retainability around the affected site, but are liable to cause an interaction with the main drug and, therefore, they have a drawback of lowering the stability of the main drug at times. For example, mixing a certain basic drug with carboxyvinyl polymers causes coloring, precipitating or lowering the release of the main drug at times. Furthermore, in order to enhance the retainability of the suppository, it is necessary to elevate the viscosity of the gel by combining a base component for neutralization of the carboxyvinyl polymers and in this case, some of the drugs are reacted with the base component to cause coloring or precipitating.

Thus, use of carboxyvinyl polymers as a suppository base has a problem that only a limited number of drugs can be applied. An object of the present invention is to provide a novel suppository base which has little interaction with the drug, and has an excellent retainability.

DISCLOSURE OF THE INVENTION

As a result of various studies in order to solve the above problem, the present inventors have found that a suppository that can contain various kinds of drugs and has a high retainability can be obtained by combining a suppository base with a hydrophobic hydroxypropyl methylcellulose in place of conventional carboxyvinyl polymers.

That is, the present invention is directed to a suppository comprising a hydrophobic hydroxypropyl methylcellulose.

It is known that hydrophobic hydroxypropyl methylcellulose can be used as a base of external preparations for skin use or gel preparations for periodontal use as described in JP-A-4-74108, JP-A-3-223301 and JP-A-6-166614, but it has not been known that hydrophobic hydroxypropyl methylcellulose can be combined in suppositories.

The hydrophobic hydroxypropyl methylcellulose in the present invention refers to hydroxypropyl methylcellulose (HPMC) into which a small amount of a long chain alkyloxyhydroxypropoxyl group has been introduced to impart a hydrophobic property to the HPMC. Here, the long chain alkyl group as a part of the alkyloxyhydroxypropoxyl group refers to a straight or branched chain alkyl group having 6 to 26 carbon atoms, and specific examples thereof are a stearyl group, a palmityl group, a myristyl group and a lauryl group. The most preferred long chain alkyloxyhydroxypropoxyl group in such hydrophobic hydroxypropyl methylcellulose is a stearyloxyhydroxypropoxyl group.

The properties of the hydrophobic hydroxypropyl methylcellulose in the present invention vary largely depending on the amount and molecular weight of the long chain alkyloxyhydroxypropoxyl group introduced. Preferred are hydrophobic hydroxypropyl methylcelluloses having a viscosity of 70–250 $mm^2/s$ (determined with Ubbelohde viscometer, at 25° C., 0.5 W/W %, a mixture of water and isopropanol (6:4 W/W)). When the viscosity is less than 70 $mm^2/s$, the retainability of the suppository may be insufficient, and when the viscosity exceeds 250 $mm^2/s$, it may be difficult to formulate the hydrophobic hydroxypropyl methylcellulose into a preparation.

The hydrophobic hydroxypropyl methylcellulose comprises preferably 0.1–20% by mass, and especially preferably 0.5–5% by mass of the preparation. In case the hydrophobic hydroxypropyl methylcellulose comprises less than 0.1% by mass, since sufficient viscosity cannot be obtained, the retainability is insufficient. In case the hydrophobic hydroxypropyl methylcellulose comprises more than 20% by mass, it will be difficult to produce the preparation because the workability is bad due to the high viscosity.

Introduction of a long chain alkyloxyhydroxypropoxyl group into HPMC can be made by a method of reacting an alkyloxyhydroxypropoxylating agent (e.g., a halide, an epoxide or an isocyanate) with the BPMC.

The thus-obtained hydrophobic hydroxypropyl methylcellulose is dispersed into an ordinary suppository base to form a gelling base.

The ordinary suppository base to be used includes oleophilic bases and water-soluble bases, and they can be used in combination. The oleophilic bases include cacao butter, lanolin fat and hard fats. The hard fats include, for example, Witepsol (tradename, manufactured by Huls Inc.), Suppocire (tradename, manufactured by Gattefosse Inc.), Isocacao (tradename, manufactured by Kao Corp.), Pharmasol (tradename, manufactured by NOF Corp.), etc. The water-soluble bases include Macrogol.

The suppository of the present invention can be prepared by a method comprising melt-mixing an ordinary suppository base with a hydrophobic hydroxypropyl methylcellulose, uniformly mixing this mixture with a drug and additives, and filling the resulting mixture into a container, a mold or the like, and cold-solidifying the filling. The method for mixing to be used is any conventional method.

BEST MODE FOR CARRYING OUT THE INVENTION

The present invention is illustrated in more detail by the following examples and experiments. The hydrophobic hydroxypropyl methylcellulose used in the Examples is Sangelose 60L (tradename, manufactured by Sankyo Chemicals Co.), i.e., a hydroxypropyl methylcellulose into which a stearyloxyhydroxypropoxyl group has been introduced.

EXAMPLE 1

| | |
|---|---:|
| Tetrahydrozoline hydrochloride | 1 g |
| Lidocaine | 60 g |
| Hydrocortisone acetate | 5 g |
| Allantoin | 20 g |
| Tocopherol acetate | 60 g |
| Light anhydrous silicic acid | 20 g |
| Hydrophobic hydroxypropyl methylcellulose | 75 g |
| Pharmasol B115 (tradename) | 1409 g |

In the heat-melted (50–70° C.) Pharmasol B115 (base) were successively dispersed the other components while stirring. After cooling to about 40° C., the mixture was filled into suppository containers and cold-molded to obtain suppositories.

EXAMPLE 2

| | |
|---|---:|
| Phenylephrine hydrochloride | 2 g |
| Dibucaine | 3 g |
| Hydrocorlisone acetate | 2 g |
| Zinc oxide | 66 g |
| Light anhydrous silicic acid | 66 g |
| Hydrophobic hydroxypropyl methylcellulose | 70 g |
| Pharmasol B115 (tradename) | 1441 g |

The same procedures as in Example 1 were repeated with the above formulation to obtain suppositories.

EXAMPLE 3

| | |
|---|---:|
| Naphazoline hydrochloride | 1 g |
| Lidocaine | 60 g |
| Prednisolone acetate | 1 g |
| Allantoin | 20 g |
| Tocopherol acetate | 60 g |
| Hydrophobic hydroxypropyl methylcellulose | 80 g |
| Witepsol H15 (tradename: base) | 1428 g |

The same procedures as in Example 1 were repeated with the above formulation to obtain suppositories.

EXAMPLE 4

| | |
|---|---:|
| Naphazoline hydrochloride | 1 g |
| Lidocaine | 60 g |
| Hydrocortisone acetate | 5 g |
| Diphenhydrarnine hydrochloride | 10 g |
| Allantoin | 20 g |
| Tocopherol acetate | 50 g |
| Zinc oxide | 100 g |
| Hydrophobic hydroxypropyl methylcellulose | 70 g |
| Witepsol H15 (tradename: base) | 1334 g |

The same procedures as in Example 1 were repeated with the above formulation to obtain suppositories.

EXAMPLE 5

| | |
|---|---:|
| Tetrahydrozoline hydrochloride | 1 g |
| Lidocaine | 60 g |
| Prednisolone acetate | 1 g |
| Crotamiton | 50 g |
| Chlorhexidine hydrochloride | 5 g |
| Aluminum chlorohydroxy allantoinate | 5 g |
| Tocopherol acetate | 50 g |
| Hydrophobic hydroxypropyl methylcellulose | 65 g |
| Witepsol W35 (tradename: base) | 1413 g |

The same procedures as in Example 1 were repeated with the above formulation to obtain suppositories.

EXAMPLE 6

| | |
|---|---:|
| Tetrahydrozoline hydrochloride | 0.1 g |
| Chlorphenylamine maleate powder | 0.4 g |
| Chlorhexidine hydrochloride | 0.5 g |
| Rydrocortisone acetate | 0.5 g |
| Allantoin | 2.0 g |
| Lidocaine | 6.0 g |
| Vitamin E acetate | 6.0 g |
| L-menthol | 1.0 g |
| Hydrophobic hydroxypropyl methylcellulose | 6.5 g |
| Aerosil 200 (tradename) | 2.0 g |
| Witepsol E85 (tradename) | 28 g |
| Witepsol W35 (tradename) | 112 g |

The same procedures as in Example 1 were repeated with the above formulation to obtain 100 suppositories.

Comparative Example 1

The same procedures as in Example 1 were repeated with the same formulation as in Example 1 except that the hydrophobic hydroxypropyl methylcellulose was replaced with carboxyvinyl polymer in the same amount as that of the hydrophobic hydroxypropyl methylcellulose to obtain suppositories for comparison.

Experiment 1 In Vitro Retaining Test

The retainability of suppositories was determined according to the method of Setnikar-Fantelli (J. Pharm. Pharmac., 1971, 23, 490–494). Thus, a cellulose membrane tube was placed in the interior of a glass vessel. A suppository was inserted into the lower part of the cellulose membrane tube, and then the tube was occlusively tied by thread under the suppository, after which the glass tube was filled with water at 37° C., whereby the water pressure acted as a force to move the drug upward. The weight of the suppository which remained in the lower part of the cellulose membrane tube was determined to evaluate the retainability of the suppository.

The suppositories of Example 1 and Comparative Example 1 were used as test samples. The weights of the suppositories were determined in a section of 0–10 cm after 10, 30 and 60 minutes, the remaining rates were calculated, and the results are shown in Table 1.

TABLE 1

| | In vitro retaining test | |
|---|---|---|
| | Weight percent of Suppository | |
| Time (mm.) | Example 1 | Comparative Example 1 |
| 10 | 97.7 | 96.8 |
| 30 | 98.0 | 97.0 |
| 60 | 98.5 | 97.0 |

It is apparent from the above table that the suppository of the present invention exhibits a retainability as high as the suppository prepared from a conventional carboxyvinyl polymer.

Experiment 2

The stability of chlorphenylamine maleate used in the suppository of Example 6 was determined.

Samples were stored at 5° C., room temperature and 35° C. for one month, the residual amounts of chlorphenylamine maleate in the samples were determined according to an HPLC method. As a result, there were obtained high residual amounts, i.e., 100.6%, 99.8% and 99.2% at 5° C., room temperature and 35° C., respectively.

The present invention makes it possible to provide an excellent suppository which can contain various kinds of drug and can retain the preparation around the affected site when administered.

What is claimed is:

1. A suppository comprising a hydrophobic hydroxypropyl methylcellulose having a long chain alkyloxyhydroxypropoxyl group, wherein the long chain alkyl of the alkyloxyhydroxypropoxyl group is a straight or branched chain alkyl group having 6 to 26 carbon atoms.

2. The suppository according to claim 1 wherein the hydrophobic hydroxypropyl methylcellulose comprises 0.1 to 20% by mass of the suppository.

3. The suppository according to claim 1 wherein the hydrophobic hydroxypropyl methylcellulose is a hydroxypropyl methylcellulose having a stearyloxyhydroxypropoxyl group.

4. The suppository according to claim 1 wherein the alkyl of the alkyloxyhydroxypropoxyl group is selected from the group consisting of stearyl, palmityl, myristyl and lauryl.

5. The suppository according to claim 1 wherein said hydrophobic hydroxypropyl methyl cellulose has a viscosity of 70–250 $mm^2/s$.

6. The suppository according to claim 1 further comprising a base component selected from the group consisting of coco butter, lanolin fat, hard fats and Macrogol.

7. The suppository according to claim 1 further comprising a base component selected from the group consisting of coco butter, lanolin fat, hard fats and Macrogol.

\* \* \* \* \*